(12) United States Patent
Islam et al.

(10) Patent No.: US 9,989,514 B2
(45) Date of Patent: Jun. 5, 2018

(54) POLY BAG AND POLYWRAP DETECTION SYSTEM

(71) Applicants: Mohammed Islam, Ellicott City, MD (US); Guillaume Lacalmontie, Elkridge, MD (US); Eric Ducharne, Laurel, MD (US)

(72) Inventors: Mohammed Islam, Ellicott City, MD (US); Guillaume Lacalmontie, Elkridge, MD (US); Eric Ducharne, Laurel, MD (US)

(73) Assignee: Postis LLC, Halethorpe, MD (US)

( * ) Notice: Subject to any disclaimer, the term of this patent is extended or adjusted under 35 U.S.C. 154(b) by 293 days.

(21) Appl. No.: 14/926,870

(22) Filed: Oct. 29, 2015

(65) Prior Publication Data

US 2016/0231226 A1 Aug. 11, 2016

Related U.S. Application Data

(60) Provisional application No. 62/072,104, filed on Oct. 29, 2014.

(51) Int. Cl.
| | | |
|---|---|---|
| *G01N 33/44* | (2006.01) | |
| *G01N 3/303* | (2006.01) | |
| *G01N 21/00* | (2006.01) | |
| *G01N 21/86* | (2006.01) | |
| *B41J 29/38* | (2006.01) | |
| *B41J 29/393* | (2006.01) | |

(52) U.S. Cl.
CPC ........... *G01N 33/442* (2013.01); *G01N 3/303* (2013.01); *G01N 2203/0039* (2013.01)

(58) Field of Classification Search
CPC ............... G01N 33/442; G01N 3/303; G01N 2203/0039; G01N 21/00; G01N 21/86; B41J 11/003; B41J 11/009; B41J 11/42; B41J 13/0063; B41J 29/38; B41J 29/393
USPC ............................. 73/9, 12.01, 12.04, 12.09
See application file for complete search history.

(56) References Cited

U.S. PATENT DOCUMENTS

| | | | | |
|---|---|---|---|---|
| 5,725,720 | A * | 3/1998 | Micaletti | B07C 1/16 156/363 |
| 2007/0176348 | A1 * | 8/2007 | Schererz | B65H 31/06 271/3.12 |

OTHER PUBLICATIONS

ASTM Standard, Designation: D 256-02e1, Standard Test Methods for Determining the Izod Pendulum Impact Resistance of Plastics, Sep. 2002.*

* cited by examiner

*Primary Examiner* — Manish S Shah
*Assistant Examiner* — Suman K Nath
(74) *Attorney, Agent, or Firm* — Baker Donelson, PC; Royal W. Craig (57) ABSTRACT

A system for detecting Poly-Bag and Poly Wrap on mail pieces, intended to be a sub-assembly on a mail unit open system that automatically opens wrapped bundles of either letter or flat mail. The system generally includes two orthogonally-opposed but otherwise identical Poly Bag Detectors both controlled by a programmable controller and deploying a swinging pendulum test, plus a Poly Wrap detector employing a rolling friction wheel test.

8 Claims, 9 Drawing Sheets

POLY BAG AND POLYWRAP DETECTION SYSTEM

CROSS-REFERENCE TO RELATED APPLICATION(S)

The present application derives priority from U.S. provisional application Ser. No. 62/072,104 filed 29 Oct. 2014.

BACKGROUND OF THE INVENTION

1. Field of the Invention

The present invention relates generally to material handling and unit opening automation systems and, more particularly, to a system that is intended to process flat-shaped mail, including envelopes, newspapers, catalogs, magazines, and other publications that meet U.S. postal service size and flexibility standards, which are secure in a bundle.

2. Description of the Background

There are various shapes, materials, and bindings used to bundle a group of printed matter. The U.S. Postal Service receives mail from business mailers and printers in bundled form, opens the bundles into individual pieces, and delivers each piece to its individual destination. The bundles vary by 1) binding type, which could be straps, string, rubber bands, or other material wrapped once, twice or more around the bundle or 2) polywrap mailing film around the bundle. Additionally, the individual mail pieces can be enclosed within a poly (plastic) bag for various reasons such as security, protection from damage, privacy, etc. After bundles are delivered to the U.S. Postal Service, the U.S. Postal Service must open each bundle, being careful not to damage the mail pieces, and prepare for sorting and delivery.

Over the past 5-10 years, the Postal Service has purchased different mail sorting equipment that has had the impact of consolidating mail bundles to certain sort points across the country, which means that more bundle opening is required.

The USPS contracted with Northrop Grumman and other vendors to design and construct a flats sequencing system (FSS). The purpose of the FSS was to automate the sequencing of flat mail for the purpose of reducing costs, absorbing growth and stabilizing postage rates. The FSS was introduced in 2008 but has been plagued by problems ever since. The FSS uses a dual pass sort technique. The first pass determines the address information, learns how many letters are to be sent to each delivery point, and starts the sorting process. During the second pass, mail from the original output is resequenced according to DPS. The USPS's $1.4 billion investment in FSS was supposed to revolutionize the labor-intensive process of delivering catalogs, magazines, newspapers, and other flat mail, but the system is still plagued by machine downtime, late deliveries, and other problems.

As a result of this, the Postal Service has expressed interest in a new technology that can automatically open bundles in order to positively impact their labor costs.

This patent presents a subsystem including method and apparatus to detect the mail bundle's wrapping material (for individually bagged items, e.g., poly bag and/or polywrap) around the outside of the individual pieces to form a bundle. The present subsystem is intended to support a mail unit open system that automatically opens wrapped bundles of either letter or flat mail.

SUMMARY OF THE INVENTION

It is an object of the invention to provide a method for detecting the type of wrapping/material on a mail bundle, which can be used to determine the appropriate handling of that particular bundle.

It is another object to provide a detection system which is small and economical such that it can be implemented within existing processes.

In accordance with the foregoing objects, the present invention generally provides a system for detecting Poly-Bag and Poly Wrap on mail pieces. The present system is well-suited to be a sub-assembly on a mail unit open system that automatically opens wrapped bundles of either letter or flat mail. The system generally includes two orthogonally-opposed bat otherwise identical Poly Bag Detectors both controlled by a programmable controller and deploying a swinging pendulum test, plus a Poly Wrap detector employing a rolling friction wheel test.

The present invention is described in greater detail in the detailed description of the invention, and the appended drawings. Additional features and advantages of the invention will be set forth in the description that follows, will be apparent from the description, or may be learned by practicing the invention.

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENT

Reference will now be made in detail to preferred embodiments of the present invention, examples of which are illustrated in the accompanying drawings. Where the same reference numbers are used throughout the drawings they refer to the same or like parts.

Figure 1:
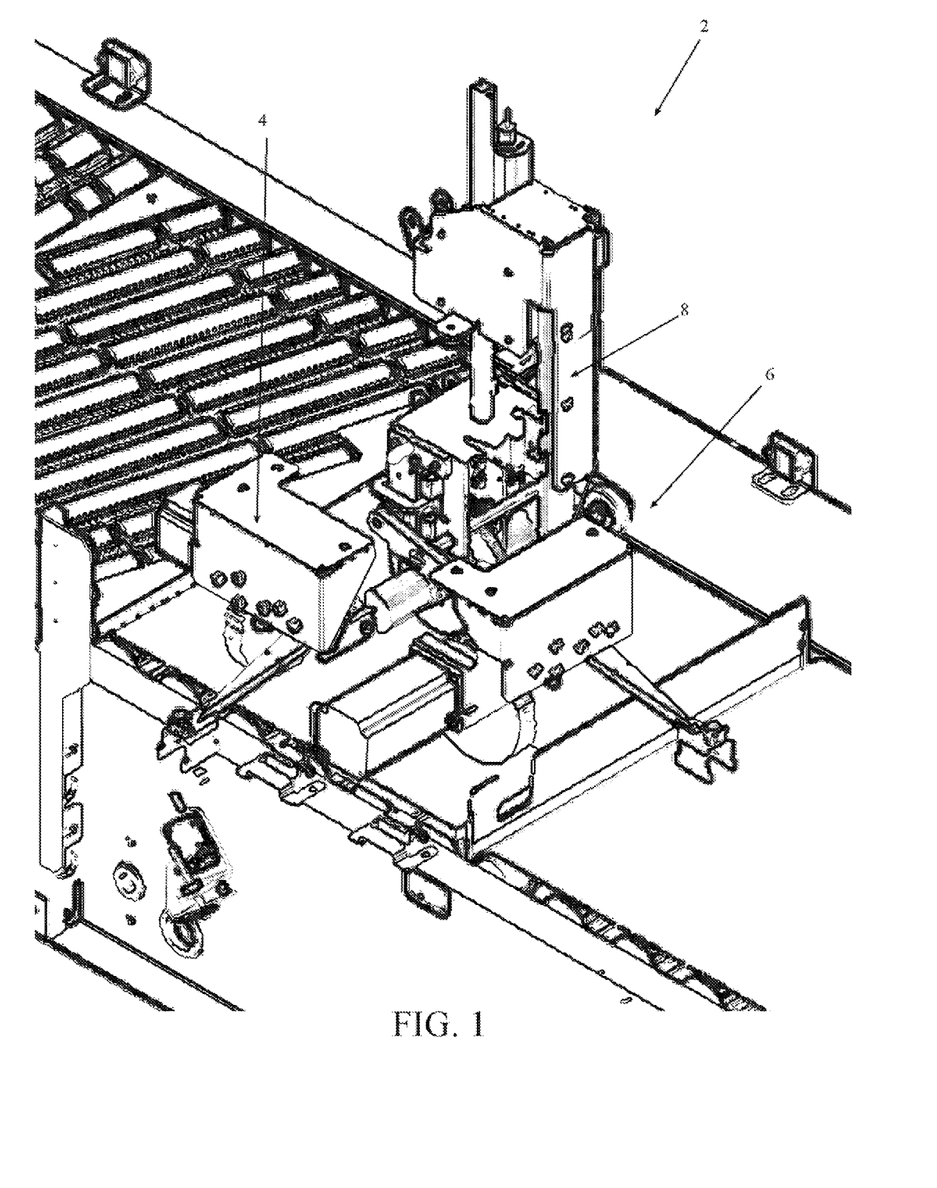
FIG. 1 is a perspective view of the apparatus to detect bundle wrapping material according to the present invention.

As shown in FIG. 1, an exemplary subsystem 2 for Poly-Bag and Poly Wrap detection according to an embodiment of the invention is illustrated. The Poly-Bag and Poly Wrap subsystem 2 is a sub-assembly intended to support a mail unit open system that automatically opens wrapped bundles of either letter or flat mail. In this context the subsystem 2 is shown as part of a roller-conveyor to handle bundled mail. However, one skilled in the art will understand that the present apparatus and method can equally be used on other "non-mail" items to determine material characteristics such as boxes, bags, or the like. The illustrated embodiment of system 2 includes two orthogonally-opposed but otherwise identical Poly Bag Detectors 4, 6, and a Poly Wrap Detector 8, all controlled by a programmable controller. A suitable controller includes a microprocessor, memory (e.g. RAM), a bus which couples the processor and the memory, a non-transitory storage device (ROM or a magnetic hard disk or an optical storage disk) coupled to the processor and the memory, a network interface card, wireless network card, or other interface device capable of wired, fiber optic, or wireless data communications with each Poly Bag Detectors 4, 6, and a Poly Wrap Detector 8. Alternatively, one skilled in the art will appreciate that when subsystem 2 is indeed part of an overall roller-conveyor system to handle bundled mail, the existing conveyor system will suffice. The systematic and redundant approach enables the individual components to leverage each other, ensures all detection results for a single piece can be compared, and eliminates duplicate components.

Figure 2:
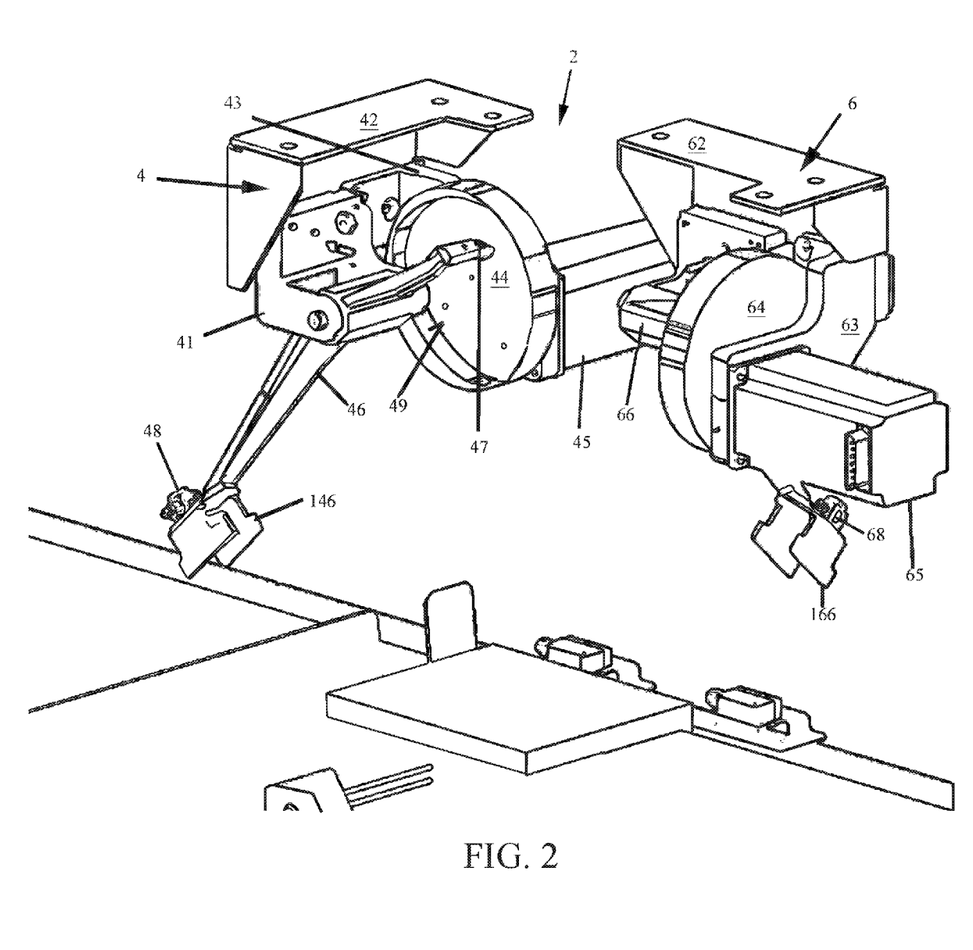
FIG. 2 is a perspective isolated view of two Poly-Bag detectors 4, 6 of the present invention (configured for front and right side detection).

FIG. 2 is a perspective isolated view of the Poly-Bag detectors 4, 6 of the present invention, which are two similar yet independent detectors. Poly Bag Detector 4 is configured to detect the front of a mail bundle and Poly Bag Detector 6 being configured for detecting a side of the mail piece. By testing both "a side" and "a front or end" of a mail bundle parked beneath, the two Poly-Bag detectors 4, 6 ensure that any polybags (comprising a tube of poly material shrink-wrapped onto the mail bundle leaving two uncovered ends) is still detected. One skilled in the art will readily understand that just a single detector can be used and the bundle can be repositioned. Also, more than two detectors can be used for additional results.

Front Poly Bag Detector 4 generally comprises an overhead mounting bracket 42 supporting both a yoke 41 and a flange 43 in an offset relationship. An annular positioning cam 44 is rotatably mounted on the flange 43 and is directly driven by a servo motor 45 that is in electronic communication with the programmable controller, e.g., the existing system controller. An impact arm 46 is pivotally mounted in yoke 41 and extends on both sides thereof, one side running to the positioning cam 44 and the other toward the conveyor. Positioning cam 44 includes a recessed hub with a surrounding rim that presents a raised track profile 49. The inner surface elevation of the rim is varied to vary the track profile 49. The distal end of impact arm 46 wields an inwardly-angled cam bearing follower 47 that engages the raised track profile 49 of positioning cam 44. The other end of impact arm 46 extends to a contact appendage 146 carrying an accelerometer 48 on its non-contact side. Side Poly Bag Detector 6 generally comprises the same array of components oriented orthogonally to Detector 4, including overhead mounting bracket 62 supporting both a yoke 61 and a flange 63 in an offset relationship. A positioning cam 64 is rotatably mounted on the flange 63 and is directly driven by a servo motor 65 that is in electronic communication with the programmable controller. An impact arm 66 is pivotally mounted in yoke 61 and extends on both sides thereof, one side running to the positioning cam 64 and the other toward the conveyor. Positioning cam 64 includes a recessed hub with a raised track profile 69. The distal end of impact arm 66 bears an inwardly-angled cam bearing follower 67 that engages the raised track profile 69 of positioning cam 64. The other end of impact arm 66 extends to a contact appendage 166 bearing an accelerometer 68 on its non-contact side.

Figure 3:
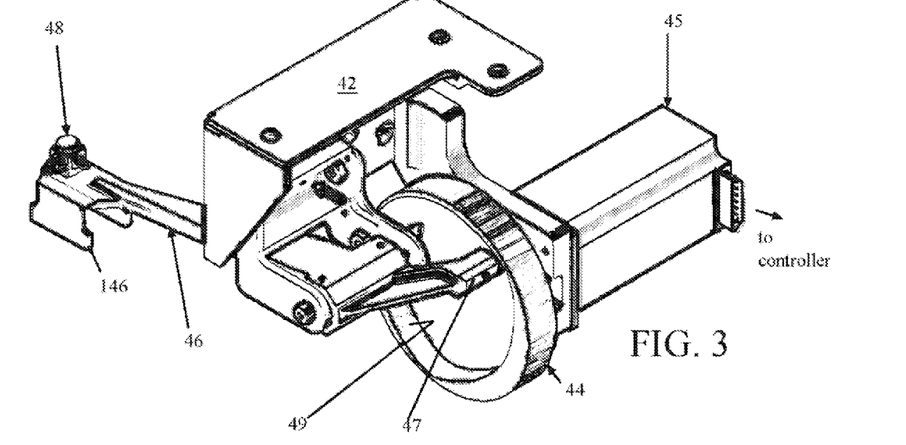
FIG. 3 is a perspective view of the Front Poly Bag Detector 4 shown in the arm "UP" or Bundle Pass position.
Figure 4:
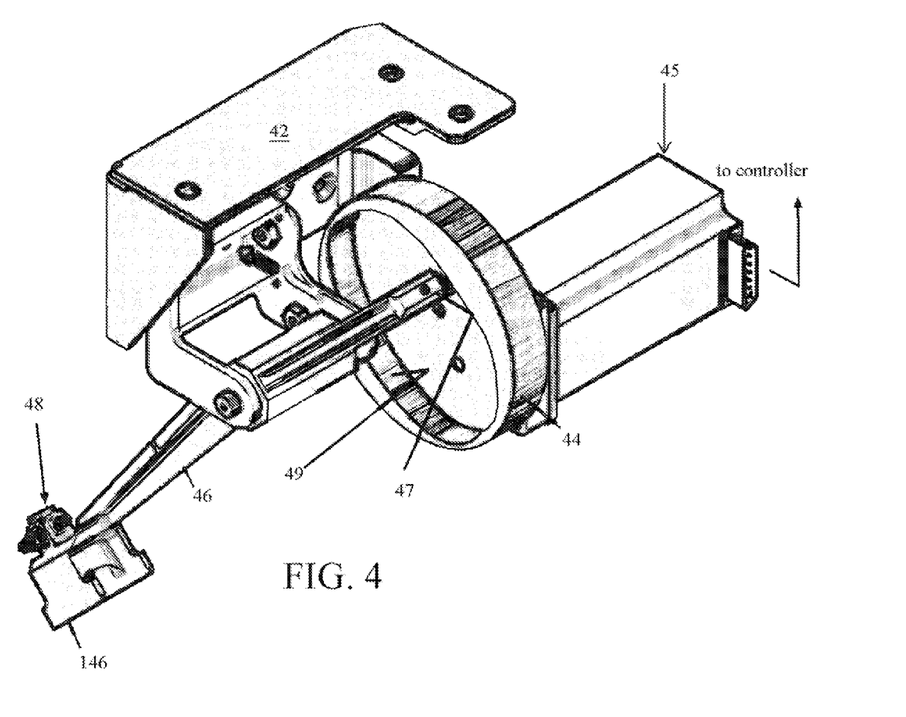
FIG. 4 is a perspective view of the Front Poly Bag Detector 4 shown in the arm "READY" position.
Figure 5:
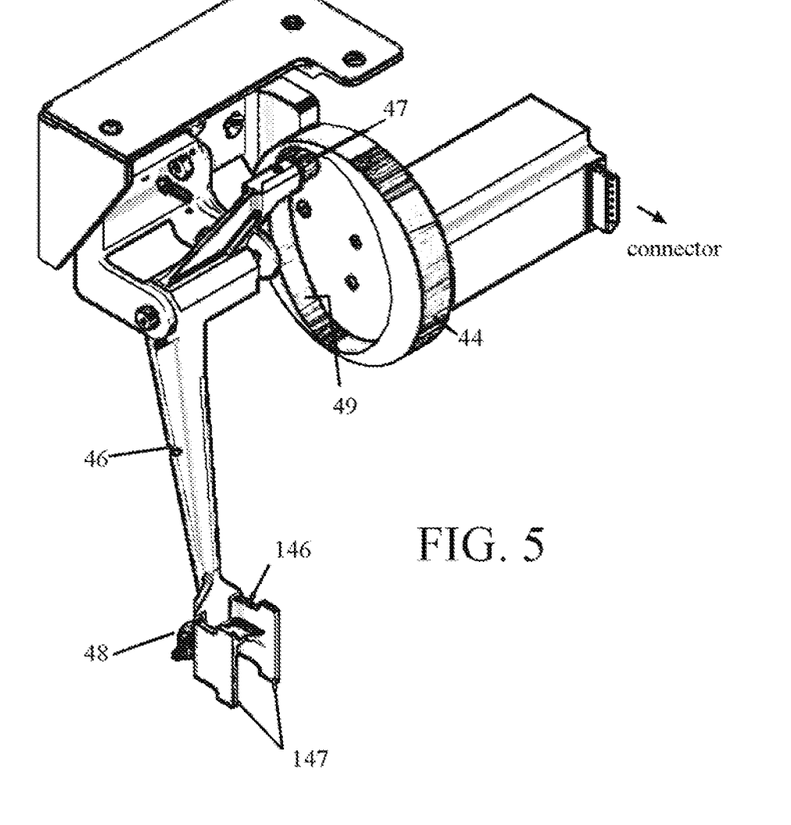
FIG. 5 is a perspective view of the Front Poly Bag Detector 4 shown in the arm "TEST" position (C).

FIGS. 3-5 form a composite view of the Front Poly Bag Detector 4, in the starting position (FIG. 3), ready position (FIG. 4), and test position (FIG. 5). The Positioning Cam 44 facilitates a simple rotating mechanism with single direction rotation, non-precise positioning, and no sensors. The only sensor is the accelerometer 48 located on the end of the impact arm 46 preferably mo tinted on the backside of contact appendage 146.

In the starting position, shown in FIG. 3, the positioning cam 44 is rotated to the illustrated position by servo motor 45 operating under system control. The impact arm 46 is engaged to positioning cam 44 by cam hearing follower 47, which protrudes into the hub of positioning cam 44 and rides along-track profile 49. The track profile 49 guides the cam follower 47 as positioning cam 44 rotates and informs the position of the impact arm 46, which at FIG. 3 is illustrated in the "UP" position. In this position, the contact appendage 146 of impact arm 46 is up and bundles can pass beneath.

From the UP position, shown in FIG. 3, the positioning cam 44 is rotated by the servo motor 45 a predetermined amount to position the impact arm 46 at an angle, to the READY position, shown in FIG. 4. The angle is determined by the amount of potential energy contained within the assembly before the testing. As the impact arm 46 is released for test, by rotation of the positioning cam 44 thereby releasing the cam bearing follower 47, the force exhibited by the impact arm 46 on impact with the bundle will create acceleration (more precisely deceleration in this application) and that will be transmitted in an output signal of the accelerometer 48. The track profile 49 required to traverse the "UP", "READY" and "TEST" positions may be a single graduated ramp, or two, three or more graduated ramps for multiple cycles per revolution, in each cycle moving between a maximum height informing the UP position (FIG. 3), a predetermined medial height to inform the READY position (FIG. 4), and a sharp drop to a minimum height that frees the impact arm 46 and releases it for test (FIG. 5).

The size of the acceleration curve is dependent on the force of the fall dictated by the velocity of the impact arm 46 at impact, and similarly to the mass of the impact arm 46 and distance of fall. Accelerometers typically will have a measuring range, and generally a larger measuring range sensor results in a reduced sensitivity. Therefore, the determination of the necessary resolution for the detection is used to select the proper accelerometer range, which is then used to determine the precise angle for the "READY" position.

From the READY position, shown in FIG. 4, the positioning cam 44 is rotated by the servo motor 45 a predetermined amount, with cam follower 47 bearing against the track profile 49 of the hub, until the cam bearing follower 47 falls free to the TEST position, shown in FIG. 5. The contact appendage 146 of the impact arm 46 strikes the mail unit parked directly beneath, and the impact energy of the impact is determined from the differential height, weight, and deceleration as measured relative to the Ready position. The impact energy becomes the basis of the calculation and analysis of the present method. Poly material is resilient and has an inherent ability to deform and absorb kinetic energy upon impact, and the impact energy against poly will, differ from that against paper. The respective deceleration profiles can be distinguished.

As best seen in FIG. 5, the impact arm 46 is designed with a contact appendage 146 having two spaced contact surfaces or points 147 to ensure that it makes consistent contact on an edge even with varying bundle surfaces. One skilled in the art will readily understand that this can be modified to provide consistent contact for the particular product being tested.

As the impact arm 46 makes contact with the bundle, the accelerometer 48 senses the deceleration, including the impact and eventual dampening out of the impact arm 46 movement over time. The accelerometer 48 is likewise in electronic communication with the system controller, and the deceleration is digitally sampled over the moment of impact time at for example, a 10 kHz sampling rate, and is stored.

The digital signal of this deceleration profile is analyzed. The analysis may comprise comparing the impact profile to a known threshold, or comparing the measured impact profile to one or more predetermined impact profiles. The predetermined impact profiles may include a typical impact profile for poly-plastic sheet material and/or a typical impact profile for paper wrapping.

This signal is precise enough to determine poly bag material, bag excess, and even poly wrap material. The deceleration profile is measureable as the poly material is compressed during the impact. The measurement technique is analogous to a notched Izod test, using a swinging pendulum to measure the kinetic energy needed to deform the mail piece upon impact. However, there is no penetration of the poly wrap. Instead, the deceleration profile is characterized and compared to a known baseline. For example, by measuring the maximum deceleration rate of a deceleration profile for a given impact energy and comparing to what would be expected of poly material versus paper, the presence or absence of a Poly Bag can be detected in real time. One skilled in the art will appreciate that the comparison decision threshold may be quantitatively determined.

Figure 6:
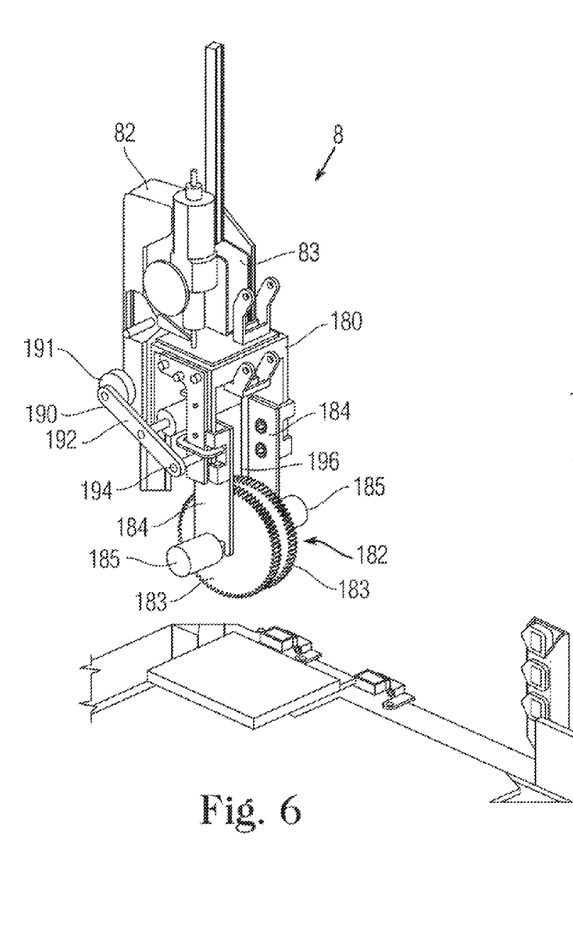
FIG. 6 is a side perspective view of Poly Wrap detector 8 shown in the "UP" or ready position (A).
Figure 7:
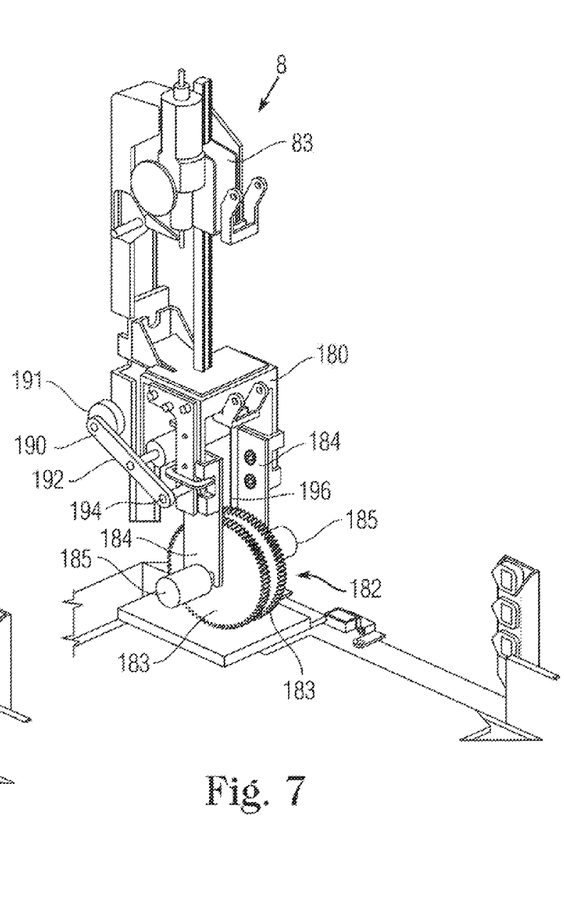
FIG. 7 is a side perspective view of Poly Wrap detector 8 shown in the "DOWN" or test position (B).

FIGS. 6-7 are perspective composite views of the Poly Wrap detector 8 of FIG. 1 in its UP position (FIG. 6) and DOWN position (FIG. 7). As seen in FIG. 6, the Poly Wrap detector 8 is mounted over the product conveyor, although it can be mounted from below or side as well.

The Poly Wrap detector 8 moves vertically, if mounted above the product, from the UP position in FIG. 6 to the DOWN position in FIG. 7, and until it makes contact with the bundle or mail piece passing beneath. Contact is made by two (2) Friction Wheels 183 that measure the contact friction of the mail piece surface.

Figure 8:
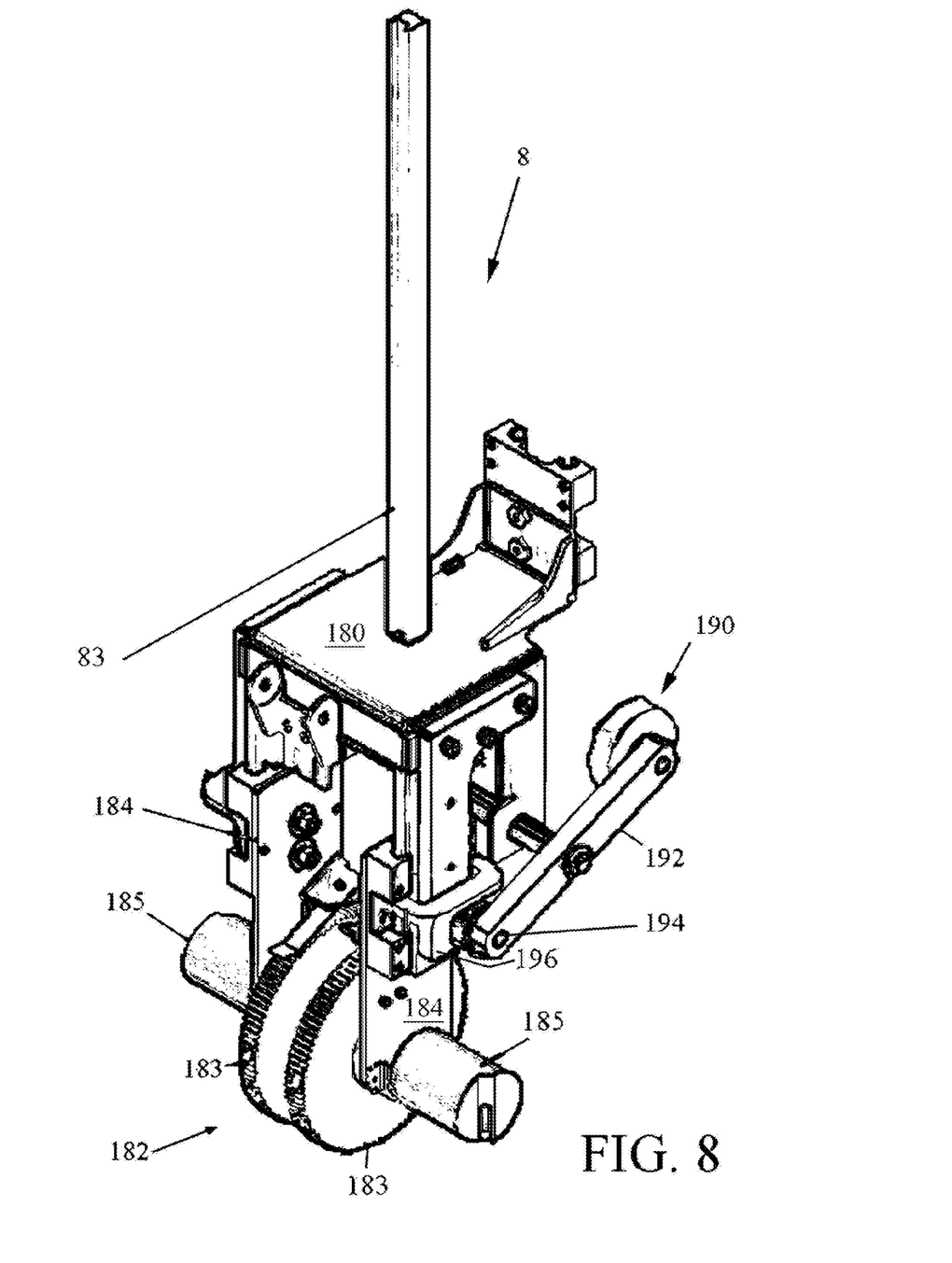
FIG. 8 is a side perspective view of Poly Wrap detector 8.
Figure 9:
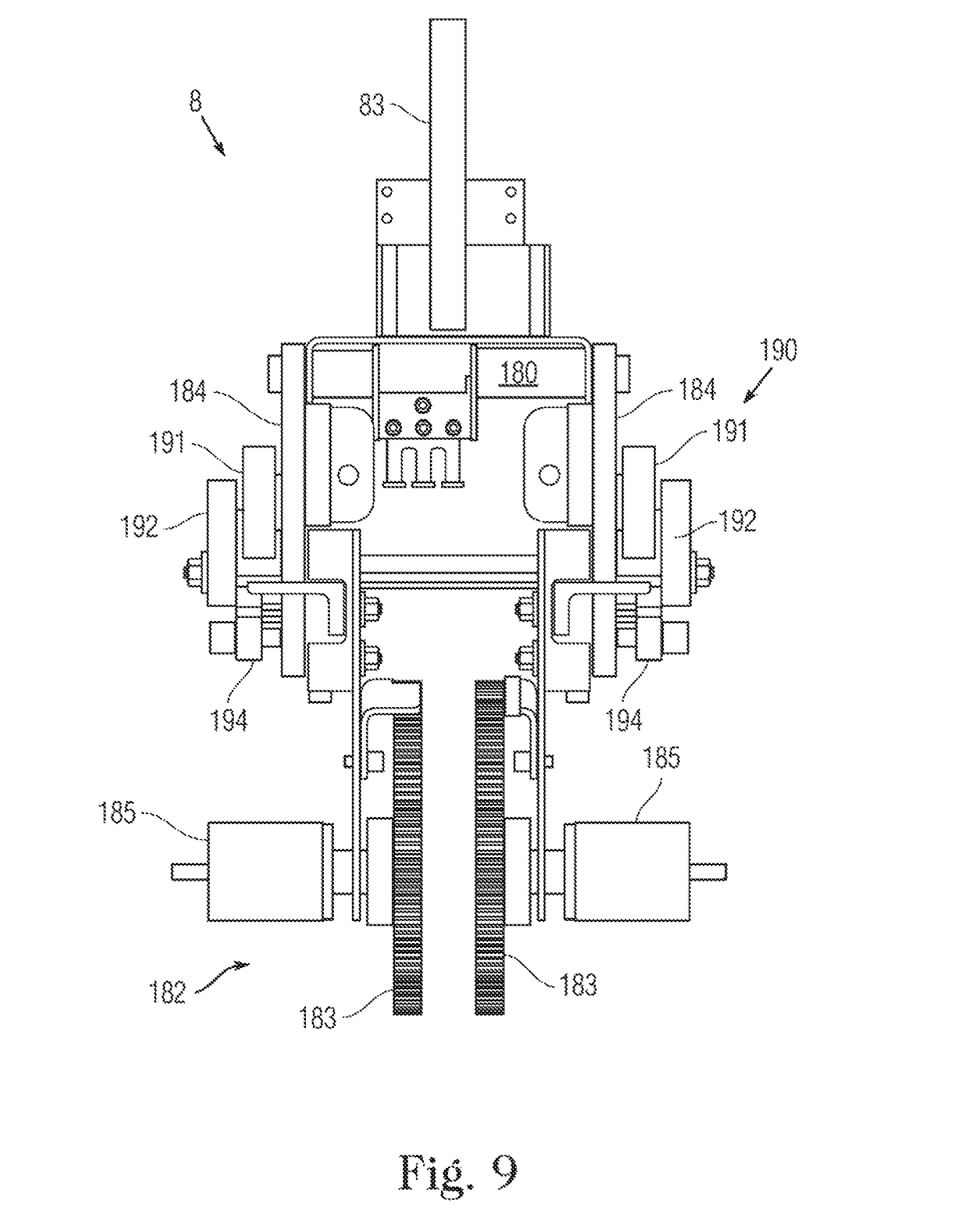
FIG. 9 is a front view of Poly Wrap detector 8.
Figure 10:
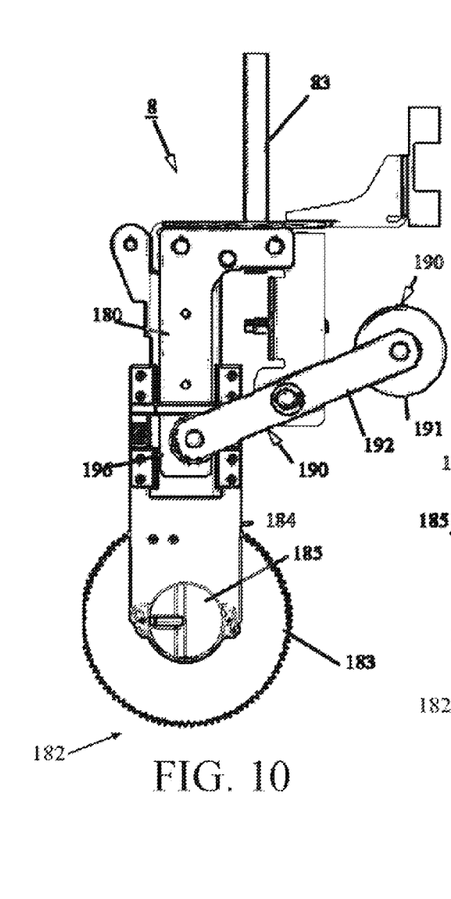
FIG. 10 is a side view of the Poly Wrap detector 8 Poly Wrap detector 8.
Figures 11, 12:
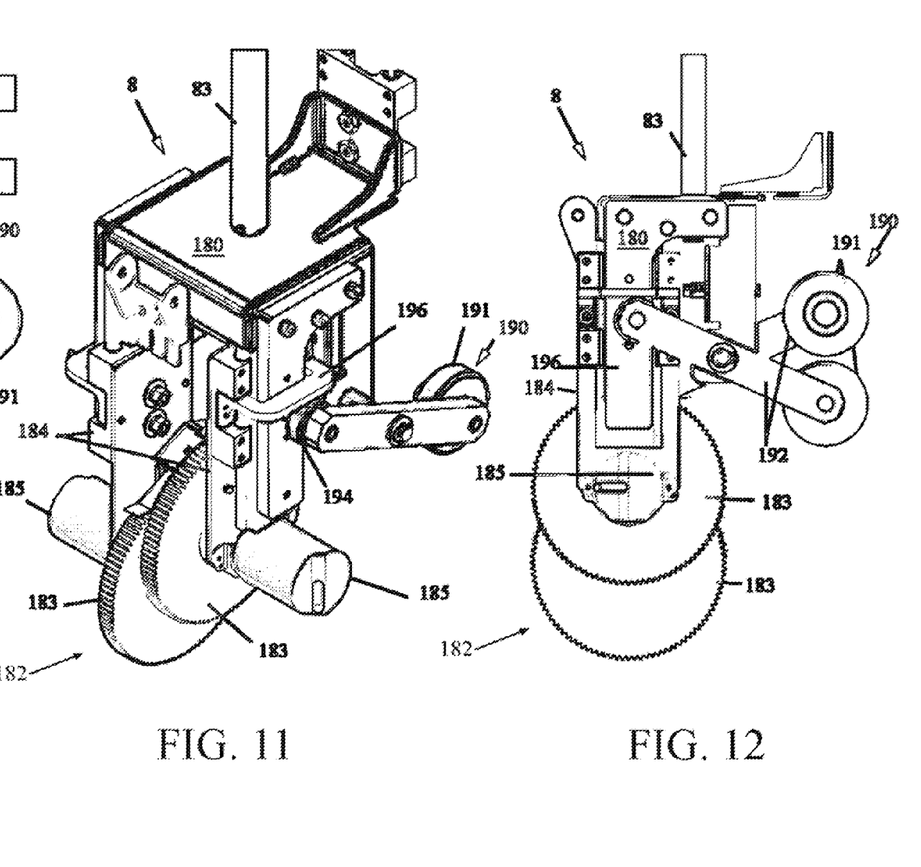
FIG. 11 is an opposite-side perspective view of the Poly Wrap detector 8.
FIG. 12 is an opposite-side view of the Poly Wrap detector 8.

FIG. 8 is a perspective isolated view of the Poly Wrap detector 8 of FIGS. 1 and 6-7, FIG. 9 is a front view, FIG. 10 is a side view, FIG. 11 is an opposite perspective view, and FIG. 12 is an opposite side view.

With collective reference to FIGS. 8-12, the Poly Wrap detector 8 comprises a linear actuator 83 driven by a servo motor 82 operating under control of the system controller. The linear actuator 83 may comprise any suitable rack and gear linear actuator, or hydraulic and/or pneumatic cylinder. The linear actuator 83 moves a sensing assembly 182 comprising two (2) Friction Wheels 183 each rotatably mounted along a common axis at the end of a suspension arm 184, both suspension arms 184 in turn being mounted on a common yoke 180. A pair of rotary encoders 185 are mounted, each opposite a respective Friction Wheel 183 and engaged thereto to provide feedback to the system controller. Each Friction Wheel 183 makes contact with the bundle. As the Friction Wheel 183 turns, the movement is measured by the respective rotary precision encoder 185. The downward force applied by the Friction Wheels 183 is maintained by a combination of assembly weight, and a vertical bearing and counter-weight assembly 190 that bears against suspension arm 184.

The vertical bearing and counter-weight assembly 190 generally comprises a counter-weight 191 mounted distally on a lever arm 192, the lever arm 192 being pivotally-mounted to the yoke 180 along its mid-section. The lever arm 192 extends to a hearing 194 that applies upward pressure to brake 196 engaged to the respective suspension arm 184.

The vertical bearing and counter-weight assembly 190 is designed to provide a consistent pressure of the Friction Wheels 183 on the bundle, thus making for a consistent amount of force and measureable movement.

The illustrated Poly Wrap detector 8 has two (2) independent detection assemblies (two vertical bearing and counter-weight assemblies 190, two friction wheels 183, and two rotary encoders 185) in order to ensure that deformations or debris (which could be in line with only one wheel) does not cause incorrect readings. The output signal of each encoder 185 is analyzed and the two results compared to make improved results. Alternatively, the Poly Wrap detector 8 could have three or more independent wheel detectors on a single assembly.

Each Friction Wheel 183 has an exterior circumference based on the precise material being detected, in order to create a definable measurement movement specific to the material of the bundle. The Friction Wheels 183 are preferably formed of a rubber material, or the like, with a high-coefficient of friction to distinguish gloss surfaces (Poly Wrap) from non-gloss (paper). Alternatively, the outer surfaces of the Friction Wheels 183 may be defined by teeth or other surface features to accurately measure poly wrap or plastic bag material.

As the bundle passes the Poly Wrap detector 8, one or both of the Friction Wheels 183 is/are caused to rotate. By controlling the variable of downward force, the amount of rotation is depending on the bundle material and the rolling friction coefficient between the Friction Wheels 183 and the bundle material. By measuring the precise rotation of the Friction Wheels 183 along the entire bundle travel, via encoders 185, analysis of the digital output signals can be performed to determine the relative differences in rolling friction for the different types of material. The encoders 185 sample angular rotation over time, and given baseline measurements this can be compared to a predetermined threshold. For example, the programmable controller may convert the angular rotation to a linear distance traveled within a time period. This can be compared to the known conveyor speed over the same time period to determine the difference. Alternately the actual coefficient of rolling friction can be computed and compared to a threshold.

The Poly Wrap detector 8 assembly also functions to provide a downward force, assisting the Poly-Bag detection process described above, by stabilizing bundles during the Poly-Bag impact and measuring, and therefore eliminate the need for an additional device to hold the bundle.

Figure 13:
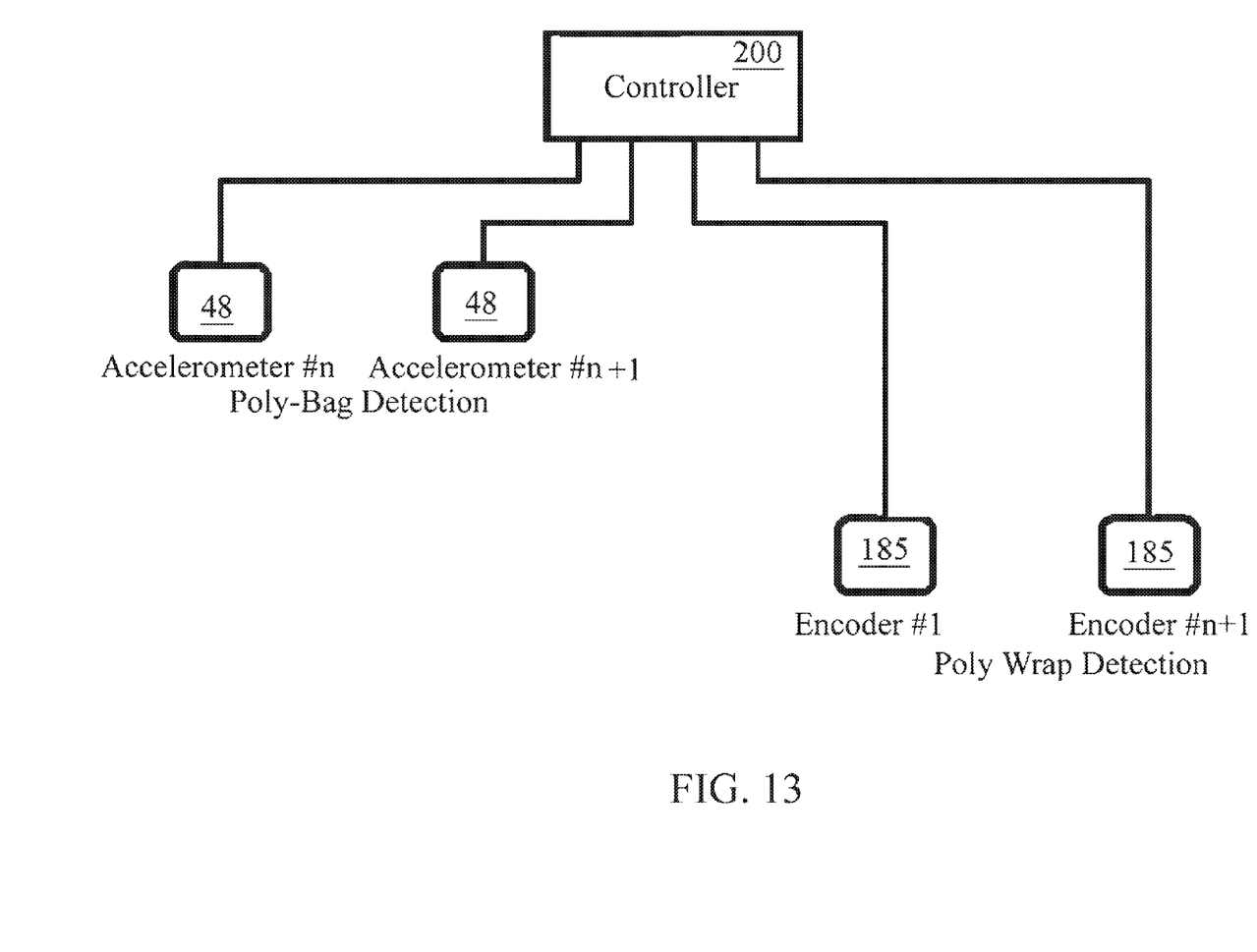
FIG. 13 is a schematic diagram of the system 2 controller architecture.

FIG. 13 is a schematic diagram of the system controller architecture. Each of the individual sensors including accelerometers 48 and encoders 385 are connected to a central Controller 200. The Controller 200 includes a programmable controller and non-transitory storage memory housing the system algorithms to decode and detect the product features. The Controller 200 may be any conventional computing device with display and user-input device, and may be the existing controller provided with the mail unit open system.

It should now be apparent that the above-described subsystem greatly assists an existing mail unit, open system toward its goal of automatically opening wrapped bundles of either letter or flat mail, by first detecting the bundles wrapping material (poly bags) and/or poly wrap around the outside of the individual pieces that form a bundle.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims, and by their equivalents.

What is claimed is:

1. A method for analyzing a mail piece and for determining if said mail piece is wrapped in poly-plastic material comprising the steps of:
    impacting said mail piece with an impact arm bearing an accelerometer;
        wherein impacting comprises contacting said mail piece with impact arm;
    measuring deceleration of said impact arm at said accelerometer during said mail piece impacting to determine an impact profile; and
    analyzing said determined impact profile and distinguishing an impact against a poly-plastic material from an impact against paper.

2. The method for analyzing a mail piece and for determining if said mail piece is wrapped in poly-plastic material according to claim 1, wherein said impact profile comprises deceleration over time.

3. The method for analyzing a mail piece and for determining if said mail piece is wrapped in poly-plastic material according to claim 1, wherein said analyzing step comprises analyzing absorption of kinetic energy of said mail piece upon impact.

4. The method for analyzing a mail piece and for determining if said mail piece is wrapped in poly-plastic material according to claim 2, wherein said sensing step comprises sampling deceleration over time.

5. The method for analyzing a mail piece and for determining if said mail piece is wrapped in poly-plastic material according to claim 4, wherein said analyzing step comprises comparing said impact profile to a threshold.

6. The method for analyzing a mail piece and for determining if said mail piece is wrapped in poly-plastic material according to claim 4, wherein said analyzing step comprises comparing said impact profile to a predetermined impact profile for poly-plastic material.

7. The method for analyzing a mail piece and for determining if said mail piece is wrapped in poly-plastic material according to claim 4, wherein said analyzing step comprises comparing said impact profile to a predetermined impact profile for paper.

8. The method for analyzing a mail piece and for determining if said mail piece is wrapped in poly-plastic material according to claim 1, further comprising the steps of,
    contacting said mail piece with at least one friction wheel,
    sensing the at least one friction wheel as it rolls along said mail piece to determine rolling friction,
    analyzing said rolling friction to distinguish a poly-plastic material from paper.

* * * * *